(12) United States Patent
Mahieux et al.

(10) Patent No.: US 8,927,800 B2
(45) Date of Patent: Jan. 6, 2015

(54) METHOD FOR REDUCING ORGANIC HALIDE CONTAMINATION IN HYDROCARBON PRODUCTS

(71) Applicants: Cedrick Mahieux, Benicia, CA (US); Sven Ivar Hommeltoft, Pleasant Hill, CA (US)

(72) Inventors: Cedrick Mahieux, Benicia, CA (US); Sven Ivar Hommeltoft, Pleasant Hill, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 16 days.

(21) Appl. No.: 13/715,845

(22) Filed: Dec. 14, 2012

(65) Prior Publication Data

US 2014/0171710 A1   Jun. 19, 2014

(51) Int. Cl.
- C07C 2/60 (2006.01)
- C07C 7/148 (2006.01)
- C07C 7/173 (2006.01)

(52) U.S. Cl.
CPC ......... C07C 7/14883 (2013.01); C07C 7/14858 (2013.01); C07C 7/173 (2013.01)
USPC ........... 585/712; 585/833; 585/851; 585/852; 585/864; 585/865; 585/866; 585/709; 585/728; 585/729; 585/727

(58) Field of Classification Search
USPC ................................................. 585/448, 712
See application file for complete search history.

(56) References Cited

U.S. PATENT DOCUMENTS

| | | | |
|---|---|---|---|
| 4,239,927 A * | 12/1980 | Brennan et al. | 585/24 |
| 4,567,315 A * | 1/1986 | Owaysi et al. | 585/827 |
| 7,476,774 B2 * | 1/2009 | Umansky et al. | 585/467 |
| 7,956,230 B2 * | 6/2011 | Timken et al. | 585/712 |
| 2007/0142215 A1 * | 6/2007 | Harris et al. | 502/53 |
| 2011/0155632 A1 * | 6/2011 | Timken et al. | 208/16 |
| 2011/0318233 A1 * | 12/2011 | Hommeltoft et al. | 422/131 |
| 2012/0024750 A1 * | 2/2012 | Zhan et al. | 208/56 |

OTHER PUBLICATIONS

Mehnert, Supported ionic liquid catalyst, Chemistry—A European Journal, 2005, 11, pp. 50-56.*
U.S. Appl. No. 13/170,948, filed Jun. 28, 2011.
Olah, et al, Friedel-Crafts Alkylatio of Anisole and Its Comparison with Toluene. Predominant Ortho-Para Substitution under Kinetic Conditions and the Effect of Thermodynamic Isomerizations, 1984, J.Am. Chem. Soc., vol. 106 No. 18 , p. 5284-5290.
Roberts, et al., New Friedel—Crafts chemistry—XXI : Alkylations with isobutyl alcohol and isobutyl chloride under "drastic" conditions, Tetrahedron vol. 25, Issue 18 pp. 4523-4528.

(Continued)

*Primary Examiner* — In suk Bullock
*Assistant Examiner* — Youngsul Jeong
(74) *Attorney, Agent, or Firm* — Susan M. Abernathy

(57) ABSTRACT

We provide a method for making hydrocarbon products with reduced organic halide contamination, comprising:
- a. separating an effluent from an ionic liquid catalyzed hydrocarbon conversion reaction into:
  - i. a hydrocarbon fraction comprising an organic halide contaminant and from greater than zero to less than 5000 wppm olefins; and
  - ii. a used ionic liquid catalyst fraction comprising a used ionic liquid catalyst; and
- b. contacting the hydrocarbon fraction with an aromatic hydrocarbon reagent and an ionic liquid catalyst to reduce a level of the organic halide contaminant to from greater than zero to 20 wppm in a finished hydrocarbon product.

30 Claims, 1 Drawing Sheet

(56) References Cited

OTHER PUBLICATIONS

Rayon, et al., MOFs as acid catalysts with shape selectivity properties New J. Chem., 2008,32, 937-940.

Brown, et al., The Action of the Catalyst Couple Aluminum Chloride—Hydrogen Chloride on Toluene at Low Temperatures; the Nature of Friedel—Crafts Complexes1,2, Jan. 1952, L.J. Snyder Ind. Eng. Chem. vol. 74, Issue 1 pp. 191-195.

DePaoli, et al., Use of Ionic Liquids in Produced Water Clean up, NGOTP Upstream Environmental Technology Review, Feb. 25, 2004.

* cited by examiner

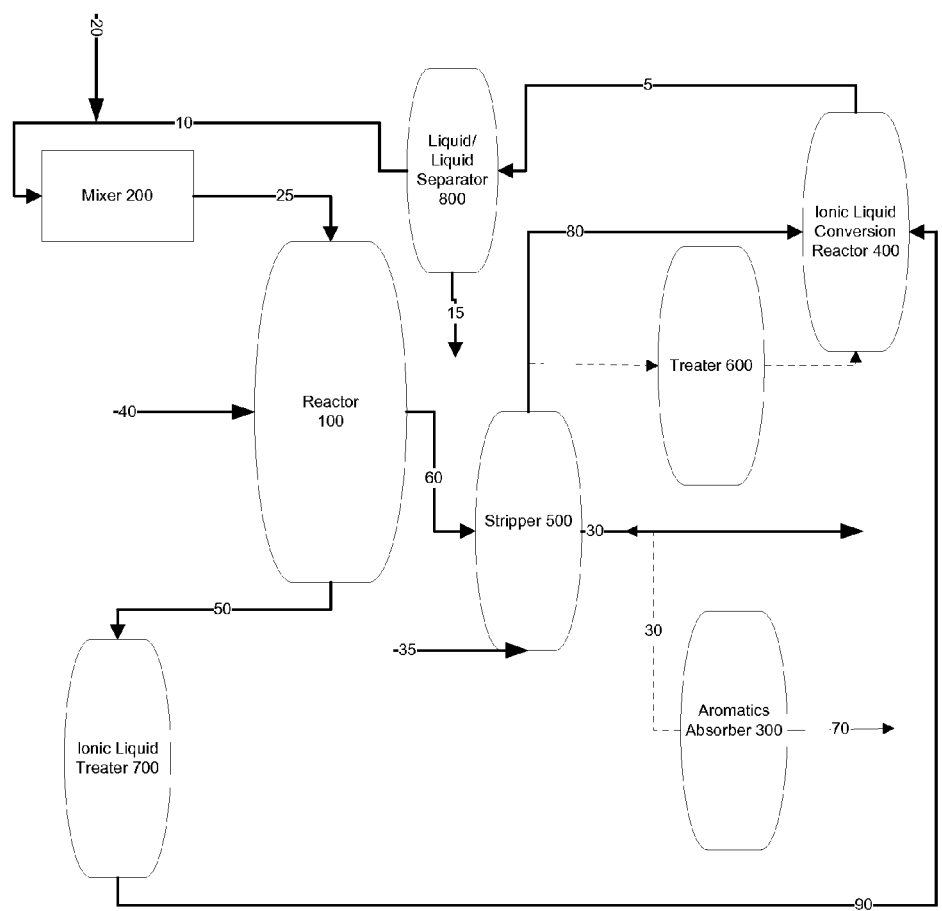

METHOD FOR REDUCING ORGANIC HALIDE CONTAMINATION IN HYDROCARBON PRODUCTS

TECHNICAL FIELD

This application is directed to a method for reducing organic halide contamination in hydrocarbon products by contacting a hydrocarbon fraction comprising an organic halide contaminant with an aromatic hydrocarbon reagent and an ionic liquid catalyst.

BACKGROUND

Alternative and improved methods for reducing organic halide contaminants in hydrocarbon products produced by ionic liquid catalyzed hydrocarbon conversion reactions are desired.

SUMMARY

This application provides a method for making hydrocarbon products with reduced organic halide contamination, comprising:
 a. separating an effluent from an ionic liquid catalyzed hydrocarbon conversion reaction into:
  i. a hydrocarbon fraction comprising an organic halide contaminant and from greater than zero to less than 5000 wppm olefins; and
  ii. a used ionic liquid catalyst fraction comprising a used ionic liquid catalyst; and
 b. contacting the hydrocarbon fraction with an aromatic hydrocarbon reagent and an ionic liquid catalyst to reduce a level of the organic halide contaminant to from greater than zero to 20 wppm in a finished hydrocarbon product.

BRIEF DESCRIPTION OF THE DRAWINGS

FIG. 1 is a diagram of a method configuration used to make hydrocarbon products with reduced organic halide contamination.

DETAILED DESCRIPTION

One or more organic halide contaminants can be present in hydrocarbon fractions separated from the effluent from an ionic liquid catalyzed hydrocarbon conversion reaction. The level of the organic halide contaminants can be greater than 25 wppm, from 50 to 5000 wppm, from 300 wppm to 8000 wppm, up to 0.1 wt %. It is desired to reduce the level of the organic halide contaminant to 20 wppm or less in a finished hydrocarbon product. Organic halides are known to cause corrosion of equipment and there are regulatory limits for organic halides in some finished hydrocarbon products. In one embodiment, the organic halide contaminant comprises organic chloride. Organic chloride can produce undesired dioxins when it is combusted.

In one embodiment, the organic halide contaminants contain alkyl chlorides relating to an olefin present in the hydrocarbon conversion reaction. In one embodiment, for example, the alkyl chloride could comprise a C3-C5 alkyl chloride. In other embodiments, the alkyl chloride can comprise a C2-C20 alkyl chloride, or mixtures thereof.

The finished hydrocarbon product made by this method can be a wide variety of different useful products, including, for example, a gasoline blending component, a middle distillate, a lubricant, a petrochemical component, or mixtures thereof. A gasoline blending component can be blended into gasoline or used directly as gasoline. Examples of gasoline blending components are naphtha and heavy naphtha. In the context of this disclosure, naphtha has a boiling range distribution less than 130° C. and heavy naphtha has a boiling range distribution from 130 to 200° C. In one embodiment, the gasoline blending component has a research octane number (RON) from 80 to 105. In one embodiment, the gasoline blending component is an alkylate gasoline.

RON is determined using ASTM D 2699-12. Additionally, the RON can be calculated from gas chromatography boiling range distribution data. The RON calculation is described in the publication, Anderson, P. C., Sharkey, J. J., 83 (1972). A "middle distillate" is a hydrocarbon product having a boiling range between 250° F. to 735° F. (121.1° C. to 390.6° C.). The term "middle distillate" includes the diesel, heating oil, jet fuel, and kerosene boiling range fractions. It can also include a portion of naphtha or light oil. In the context of this disclosure, a "lubricant" is a hydrocarbon boiling in the range of about 650° F. (343° C.) and higher. The lubricant may comprise a bright stock. Bright stock is a lubricant having a kinematic viscosity above 180 $mm^2/s$ at 40° C. Lubricants can be blended with additives and used, for example, as diluents for the additives or in finished lubricants.

The test methods used for boiling range distributions of the finished hydrocarbon products in this disclosure are ASTM D 2887-08 and ASTM D 6352-04 (2009). The test method is referred to herein as "SIMDIST". The boiling range distribution determination by distillation is simulated by the use of gas chromatography. The boiling range distributions obtained by this test method are essentially equivalent to those obtained by true boiling point (TBP) distillation (see ASTM Test Method D 2892), but are not equivalent to results from low efficiency distillations such as those obtained with ASTM Test Methods D 86 or D 1160.

Separating

The method used to reduce the level of the organic halide contaminant comprises separating the effluent from the ionic liquid catalyzed hydrocarbon conversion reaction into at least two fractions, one being a hydrocarbon fraction comprising the organic halide contaminant and from greater than zero to less than 5000 wppm olefins and the second being a used ionic liquid catalyst fraction comprising a used ionic liquid catalyst. The used ionic liquid catalyst is the ionic liquid catalyst that had been used in the ionic liquid catalyzed hydrocarbon conversion reaction. The separating can be done using any means known to those skilled in the art to effect liquid/liquid separation. Examples of separating processes that can be used are coalescence, phase separation (fractional distillation, heated distillation, non-heated distillation), extraction, membrane separation, and partial condensation. A fractionator used for the separating can, for example, comprise one or more of the following: settler, coalescer, centrifuge, distillation column, condenser, and filter. In one embodiment the hydrocarbon fraction is withdrawn hot from the bottom of a fractionator. By 'hot' is meant above ambient temperature, and can be, for example, from 30° C. to 500° C., or from 50° C. to 200° C.

The hydrocarbon fraction additionally comprises from greater than zero to less than 5000 wppm olefins. In one embodiment, the hydrocarbon fraction comprises from zero to less than 4000 wppm olefins. In one embodiment, even if olefins were a significant fraction of the reactants in the initial ionic liquid catalyzed hydrocarbon conversion reaction, the majority (up to all) of the olefins are hydrogenated, alkylated, or oligomerized such that much lower levels of olefins remain in the effluent from the ionic liquid catalyzed hydrocarbon conversion reaction.

An organic chloride contaminant level can be determined by X-ray Fluorescence Spectroscopy, e.g., ASTM D7536-09, Standard Test Method for Chlorine in Aromatics by Monochromatic Wavelength Dispersive X-ray Fluorescence Spectrometry.

The wppm of olefins can be determined by Gas Chromatography(GC)-Mass Spectroscopy, other GC methods known by those skilled in the art, or other methods known to give an accurate result for the type of sample being tested. When naphthenes are present, the wppm of olefins can be determined by acetone-d6 chemical ionization mass spectroscopy. The chemical ionization mass spectroscopy method is described in Chang S. Hsu, *Analytical Advances for Hydrocarbon Research,* 2003, pages 295-296. The wppm of olefins can also be determined by measuring the bromine number (ASTM D1159-07 (Reapproved 2012)) or bromine index (ASTM D2710-09).

The wt % Olefins can also be determined by proton-NMR by the following steps, A-D:

A. Prepare a solution of 5-10% of the test hydrocarbon in deuterochloroform.

B. Acquire a normal proton spectrum of at least 12 ppm spectral width and accurately reference the chemical shift (ppm) axis. The instrument must have sufficient gain range to acquire a signal without overloading the receiver/ADC. When a 30° pulse is applied, the instrument must have a minimum signal digitization dynamic range of 65,000. Preferably the dynamic range will be 260,000 or more.

C. Measure the integral intensities between:
  6.0-4.5 ppm (olefin)
  2.2-1.9 ppm (allylic)
  1.9-0.5 ppm (saturate)

D. Using the molecular weight of the test substance determined by ASTM D 2503, calculate:

1. The average molecular formula of the saturated hydrocarbons.
  2. The average molecular formula of the olefins.
  3. The total integral intensity (=sum of all integral intensities).
  4. The integral intensity per sample hydrogen (=total integral/number of hydrogens in formula).
  5. The number of olefin hydrogens (=Olefin integral/integral per hydrogen).
  6. The number of double bonds (=Olefin hydrogen times hydrogens in olefin formula/2).
  7. The wt % olefins by proton NMR=100 times the number of double bonds times the number of hydrogens in a typical olefin molecule divided by the number of hydrogens in a typical test substance molecule. Wt % olefins can be converted to wppm olefins by multiplying the wt % olefins result in step D by 10,000.

The wt % olefins by proton NMR calculation procedure, D, works best when the percent olefins result is low, less than about 15 wt %. The olefins must be "conventional" olefins; i.e. a distributed mixture of those olefin types having hydrogens attached to the double bond carbons such as: alpha, vinylidene, cis, trans, and tri-substituted. These olefin types will have a detectable allylic to olefin integral ratio between 1 and about 2.5. When this ratio exceeds about 3, it indicates a higher percentage of tri or tetra substituted olefins are present and that different assumptions must be made to calculate the number of double bonds in the sample.

Description of FIG. 1

One embodiment of how this method can be practiced is shown in FIG. 1. Referring to FIG. 1, an effluent from an ionic liquid catalyzed hydrocarbon conversion reaction (5) is separated by a liquid/liquid separator (800) into a hydrocarbon fraction (10) comprising the organic halide contaminant and less than 5000 wppm olefins and a used ionic liquid catalyst fraction (15). The hydrocarbon fraction (10) is mixed with the aromatic hydrocarbon reagent (20) and the mixture is passed through a mixer (200) to make mixed feed (25). The mixed feed (25) and an ionic liquid catalyst (40) are fed to a reactor (100) where the reactants are contacted. After the contacting the outflow from the reactor (60) is passed to a stripper (500). A light gas (35) is also fed to the stripper (500). The stripper removes a light fraction (80) and produces the finished hydrocarbon product (30) having a level of the organic halide contaminant of 20 wppm or less. Optionally, either a portion or the entire finished hydrocarbon product (30) is passed to an aromatics absorber (300), wherein a content of aromatics in the finished hydrocarbon product is reduced to make a finished hydrocarbon product with low aromatics (70). The light gas (80) is fed back to the ionic liquid conversion reactor (400). Optionally, the light gas (80) may be passed (either in whole or in part) first through a treater (600) to remove aromatics. The separated ionic liquid catalyst (50) from the reactor (60) is sent to an ionic liquid treater (700) to make a regenerated ionic liquid catalyst (90), which can be recycled to the ionic liquid hydrocarbon conversion reaction (400).

Contacting

The method for making hydrocarbon products with reduced organic halide contamination also comprises contacting the hydrocarbon fraction comprising the organic halide contaminant with an aromatic hydrocarbon reagent and an ionic liquid catalyst to reduce the level of the organic halide contaminant to 20 wppm or less in a finished hydrocarbon product. In one embodiment the level of the organic halide contaminant in the finished hydrocarbon after the contacting is from greater than zero to 15 wppm.

The contacting can be done at a temperature from 0° C. to 100° C., 0° C. to 150° C., or 0° C. to 200° C. In one embodiment, the contacting is done at ambient conditions and does not require any heating or cooling.

The contacting can be done at any pressure. However, the pressure will typically be chosen in such a way that the hydrocarbon fraction comprising the organic halide contaminant is in the liquid phase during the contacting.

The time for contacting is generally 24 hours or less. In one embodiment, the time for contacting is from 2 seconds to less than 1 hour. In another embodiment the time for contacting is from ten seconds to eight hours or from 0.1 minutes to 6 hours. Under some conditions, the time for contacting is from 2 to 10 seconds.

In one embodiment, the equivalents of the aromatic hydrocarbon reagent relative to the organic halide contaminant are controlled when they are mixed together or at the start of the contacting. For example, 0.3 to 40 equivalents, 0.3 to 20 equivalents, 0.3 to 10 equivalents, or 0.3 to 5 equivalents, of the aromatic hydrocarbon reagent relative to the organic halide contaminant can be mixed together. In one embodiment, 0.3 to 20 equivalents of the aromatic hydrocarbon reagent relative to an organic chloride contaminant in the hydrocarbon fraction are mixed together.

Under certain Friedel-Crafts reaction conditions, during the contacting, sub-stoichiometric amounts of the aromatic hydrocarbon reagent compared to the organic halide contaminant can be effective because polyalkylation of the aromatic hydrocarbon reagent and organic chloride occurs.

In one embodiment, the equivalents of the ionic liquid catalyst relative to the organic halide contaminant are controlled when they are mixed together. In some embodiments, the equivalents of the ionic liquid catalyst are higher than the equivalents of the aromatic hydrocarbon, both relative to the organic halide contaminant. In other embodiments, the equivalents of the ionic liquid catalyst are lower than the equivalents of the aromatic hydrocarbon, both relative to the organic halide contaminant.

In one embodiment, a temperature of the hydrocarbon fraction at a start of the contacting is 0° C. to 150° C. For example, as described previously, the hydrocarbon fraction can be withdrawn hot from a previous process, such as from a fractionator.

The aromatic hydrocarbon reagent can be any aromatic hydrocarbon that reacts during the contacting and is effective at reducing the level of the organic halide contaminant to 20 wppm or less. In one embodiment the aromatic hydrocarbon reagent comprises monocyclic aromatic hydrocarbon compounds. Monocyclic aromatic hydrocarbon compounds are benzene and benzene derivatives.

Benzene derivatives that can be used have from one to five substituents attached to a central benzene core. In one embodiment, the aromatic hydrocarbon reagent is a benzene derivative that that has from one to three substituents. Examples of benzene compounds with just one substituent are phenol, which carries a hydroxyl group; and toluene with a methyl group. When there is more than one substituent present on the ring, their spatial relationship becomes a distinguishing characteristic for which the arene substitution patterns ortho, meta, and para are used. For example, three isomers exist for cresol because the methyl group and the hydroxyl group can be placed next to each other (ortho), one position removed from each other (meta), or two positions removed from each other (para). Xylenol has two methyl groups in addition to the hydroxyl group, and, for this structure, 6 isomers exist. A mixture of monocyclic aromatic hydrocarbon compounds can be used.

Non-limiting examples of benzene derivatives are: toluene, ethylbenzene, p-xylene, m-xylene, mesitylene, durene, 2-phenylhexane, biphenyl, and phenol.

In another embodiment, the aromatic hydrocarbon reagent comprises reformate. Reformate is a product from a petroleum-refinery reforming process; types are thermal reformate (from thermal reforming), and catalytic reformate (from catalytic reforming)

In one embodiment, the aromatic hydrocarbon reagent and the hydrocarbon fraction are mixed together to make a mixed feed and the mixed feed is fed to a reactor used for the contacting. The aromatic hydrocarbon reagent and the hydrocarbon fraction can be mixed together with any mixer that provides good mixing, for example a stirrer, a shaker, a static mixer or nozzle might be employed. In another embodiment, the aromatic hydrocarbon reagent is added to a mixture of the hydrocarbon fraction and the ionic liquid catalyst either before or during the contacting.

In one embodiment, the ionic liquid catalyst is introduced to a reactor used for the contacting using one or more nozzles.

The contacting may be done in any type of reactor that is effective for reducing the level of the organic halide contaminant to 20 wppm or less in the finished hydrocarbon product. Examples of reactors that can be used for the contacting are static mixers, continuously stirred tank reactors (CSTRs), nozzle reactors (including nozzle loop reactors), tubular reactors (including continuous tubular reactors), fixed bed reactors (including fixed bed contactor reactors), and loop reactors (including static mixer loop reactors). Fixed bed contactor reactors are described in US Patent Publication US 20110318233 A1.

Fixed Bed Reactor

In one embodiment, the contacting is done in a fixed bed reactor. In this embodiment, the ionic liquid catalyst is supported on a fixed bed. The fixed bed can comprise a particulate support material. The particulate support material can serve as a solid contact material that is wetted by the ionic liquid catalyst. In one embodiment, the particulate support material can comprise a non-basic polar refractory material, such as silica, alumina, titania, zirconia, thoria, boria, niobium oxide, tin oxide, and physical and chemical mixtures thereof. In another embodiment, the fixed bed can comprise a porous solid comprising a particulate having a diameter in the longest direction from 25 to 3000 µm, such as 250 to 1000 µm. In one embodiment, the particulate support material has a diameter of 1 to 20 mm. In one embodiment, the porous solid has pores in the range of 20 to 150 Å. In one embodiment the porous solid or particulate support material is selected from the group consisting of silica, alumina, titania, zirconia, thoria, boria, niobium oxide, tin oxide, and mixtures thereof. In another embodiment, the porous solid or particulate support material can comprise polymer resins with pyridine groups, amine groups, other basic groups; or porous forms of carbon, including forms of activated carbon. For example, the porous solid or particulate support material can be protonated forms of polyvinyl pyridine crosslinked with divinyl benzene and/or polystyrene amines In one embodiment, the porous solid is able to form an adduct with the liquid catalyst and the porous solid does not react or disintegrate under operating conditions during the contacting.

In one embodiment, the particulate support material in the reactor having a fixed bed, used for the contacting, has a stronger interaction with a fresh ionic liquid catalyst than with a partially passivated ionic liquid. In this embodiment, the fixed bed can comprise a particulate support material selected from the group consisting of silica, alumina, titania, zirconia, thoria, boria, and mixtures thereof, and the particulate support material has a stronger interaction with a fresh ionic liquid catalyst than with a partially passivated ionic liquid catalyst. In these embodiments, a technical advantage is realized because the partially passivated ionic liquid catalyst can be more easily removed from a reactor used for the contacting while retaining the more active ionic liquid catalyst in the reactor.

In one embodiment, the ionic liquid catalyst is supported on a fixed bed of solid contact material that is wetted by the ionic liquid catalyst and the ionic liquid catalyst is replaced either intermittently or continuously by: a. adding fresh ionic liquid catalyst to the fixed bed of solid contact material, and b. withdrawing a partially passivated ionic liquid catalyst. The addition of fresh ionic liquid catalyst and withdrawal of partially passivated ionic liquid catalyst can be used to maintain a catalyst activity during the contacting to effectively reduce the level of the organic halide contaminant in the finished hydrocarbon product. As described above, this embodiment can also provide a longer residence time for a supported liquid catalyst (e.g., the ionic liquid catalyst) than for a mixture of the hydrocarbon fraction and the aromatic hydrocarbon reagent.

By 'partially passivated' is meant that the activity of the catalyst is at least 5% up to 95% reduced compared to the fresh ionic liquid catalyst. In one embodiment the partially passivated ionic liquid catalyst is the same as the used ionic liquid catalyst in the used ionic liquid catalyst fraction.

In one embodiment, the ionic liquid catalyst is supported on a fixed bed in a reactor, and sufficient voids remain in the reactor to provide ample flow of the hydrocarbon fraction and the aromatic hydrocarbon reagent.

One technical benefit that can be realized when the ionic liquid catalyst is supported is that some or all of the ionic liquid catalyst remains in the reactor when the finished hydrocarbon product is released from the reactor. For example, the fixed bed reactor can provide a longer residence time for the ionic liquid catalyst than for a mixture of the hydrocarbon fraction and the aromatic hydrocarbon reagent. This reduces process complexity, as less product clean-up can be needed, and there can be reduced equipment required for moving the ionic liquid catalyst. Additionally, there can be safety benefits, as when the ionic liquid catalyst remains in the reactor there is less likelihood of exposure of equipment and personnel to the ionic liquid catalyst.

Aromatic Content in Finished Hydrocarbon Product

In one embodiment, the finished hydrocarbon product has less than 1 wt % aromatics, such as less than 5,000 wppm aromatics, less than 2,500 wppm aromatics, or 5,000 wppm aromatics down to 0 wppm aromatics. In one embodiment, the finished hydrocarbon product has from 0 to 5,000 wppm aromatics. In one embodiment, these levels of aromatics can be achieved without any post treatment to reduce the aromatics in the finished hydrocarbon product. Alternatively, the method can additionally comprise passing the finished hydrocarbon product to an aromatics absorber, where a content of aromatics in the finished hydrocarbon product is reduced to below 100 wppm, to below 50 wppm, to below 25 wppm, or from 0 wppm to 25 wppm. In one embodiment, the aromatics absorber comprises activated carbon (i.e., carbon absorber). Other means to reduce the content of aromatics in the finished hydrocarbon product can also be employed.

Ionic Liquid Catalyst

Ionic liquid catalysts are very effective for catalyzing a broad range of hydrocarbon conversion reactions. Examples of hydrocarbon conversion reactions are paraffin alkylation, olefin dimerization, olefin oligomerization, concurrent alkylation and oligomerization, isomerization, and aromatic alkylation. The ionic liquid hydrocarbon conversion reaction can be one used to make gasoline blending components, middle distillates, lubricants, or petrochemical components. In one embodiment, the ionic liquid catalyzed hydrocarbon conversion reaction is an alkylation, an oligomerization, or a mixture thereof.

Ionic liquid catalysts are composed of at least two components which form a complex. The presence of the first component should give the ionic liquid catalyst a Lewis acidic character. The first component of the ionic liquid catalyst can comprise a Lewis Acid. The Lewis acid can be a metal halide compound selected from components such as Lewis Acidic compounds of Group 13 metals, including aluminum halides, alkyl aluminum halide, gallium halide, and alkyl gallium halide. Other Lewis Acidic compounds, such as Group 3, 4, and 5 metal halides, in addition to those of Group 13 metals, can also be used. Other specific examples include $ZrCl_4$, $HfCl_4$, $NbCl_5$, $TaCl_5$, $ScCl_3$, $YCl_3$, and mixtures thereof. The periodic table by the International Union of Pure and Applied Chemistry (IUPAC), version date 22 Jun. 2007, is used for defining the Groups 3, 4, 5, and 13 metals. In one embodiment the first component of the ionic liquid catalyst is aluminum halide or alkyl aluminum halide. For example, aluminum trichloride can be the first component of the ionic liquid catalyst. In one embodiment the ionic liquid catalyst includes strongly Lewis acidic anions, such as $Al_2Cl_7^-$. $Al_2Cl_7^-$, for example, is a strongly Lewis acidic anion, while $AlCl_4^-$ is not.

Generally, the greater the mole ratio of the first component to the second component, the greater is the acidity of the ionic liquid catalyst.

The second component making up the ionic liquid catalyst is an organic salt or mixture of salts. These salts can be characterized by the general formula Q+A−, wherein Q+ is an ammonium, phosphonium, boronium, iodonium, or sulfonium cation and A− is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $TaF_6^-$, $CuCl_2^-$, $FeCl_3^-$, $HSO_3^-$, $RSO_3^-$, $SO_3CF_3^-$, alkyl-aryl sulfonate, and benzene sulfonate (e.g., 3-sulfurtrioxyphenyl). In one embodiment the second component is selected from those having quaternary ammonium halides containing one or more alkyl moieties having from about 1 to about 12 carbon atoms, such as, for example, trimethylamine hydrochloride, methyltributylammonium halide, or substituted heterocyclic ammonium halide compounds, such as hydrocarbyl-substituted-pyridinium halide compounds for example 1-butylpyridinium halide, benzylpyridinium halide, or hydrocarbyl-substituted-imidazolium halides, such as for example, 1-ethyl-3-methyl-imidazolium chloride.

In one embodiment the ionic liquid catalyst is selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof. For example, the ionic liquid catalyst can be an acidic haloaluminate ionic liquid catalyst, such as an alkyl substituted pyridinium chloroaluminate or an alkyl substituted imidazolium chloroaluminate of the general formulas A and B, respectively.

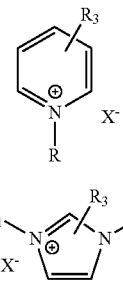

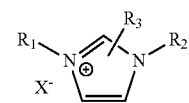

In the formulas A and B; R, $R_1$, $R_2$, and $R_3$ are H, methyl, ethyl, propyl, butyl, pentyl or hexyl group, and X is a chloroaluminate. In one embodiment the X is $AlCl_4^-$, $Al_2Cl_7^-$, or $Al_3Cl_{10}^-$. In the formulas A and B, R, $R_1$, $R_2$ and $R_3$ may or may not be the same. In one embodiment the ionic liquid catalyst is N-butylpyridinium heptachlorodialuminate $[NBuPy^+][Al_2Cl_7^-]$. In one embodiment the ionic liquid catalyst is 1-Ethyl-3-methylimidazolium heptachlorodialuminate $[emim^+][Al_2Cl_7^-]$.

In one embodiment the ionic liquid catalyst comprises a cation selected from the group of an alkyl-pyridinium, an alkyl-imidazolium, or a mixture thereof. In another embodiment the acidic ionic liquid can have the general formula $RR'R''NH^+Al_2Cl_7^-$, wherein N is a nitrogen containing group, and wherein RR' and R'' are alkyl groups containing 1 to 12 carbons, and where RR' and R'' may or may not be the same.

In one embodiment, the ionic liquid catalyst comprises less than one wt %, less than 0.5 wt %, or no, silyl-containing groups. Silyl-containing groups comprise $H_3Si-$ or hydrocarbyl derivatives thereof, e.g. $R_3Si—$. Examples of silyl-containing groups are siloxanes and silanes. Siloxanes, for example, are typically not stable in very strongly acidic media.

The used ionic liquid catalyst is the ionic liquid catalyst that is present in the effluent from the ionic liquid catalyzed hydrocarbon conversion reaction. In some embodiments, the used ionic liquid catalyst can be partially passivated. The ionic liquid catalyst used for contacting to reduce the level of the organic halide contaminant can be the same as or different from the used ionic liquid catalyst. In one embodiment, the used ionic liquid catalyst and the ionic liquid catalyst for contacting comprise the same cation. In another embodiment the ionic liquid catalyst used for contacting is a partially passivated ionic liquid catalyst. In one embodiment the ionic liquid catalyst used for contacting has a lower acidity than a more acidic ionic liquid catalyst used in the ionic liquid catalyzed hydrocarbon conversion reaction.

Stripping Out a Light Fraction

In one embodiment, the method for making hydrocarbon products with reduced organic halide contamination also comprises stripping out a light fraction comprising hydrogen halide from an outflow from a reactor used for the contacting. The stripping out can be done in a stripper, such as a stripping column, and a light gas such as methane, ethane, propane, butane, or pentane can be used to effect the stripping out. In one embodiment, the light gas can be hot butane gas such as isobutene at a temperature from 100° F. to 300° F., or 150° F. to 200° F. The light fraction comprising hydrogen halide can be recycled to another step in the method, for example it can be recycled to the ionic liquid catalyzed hydrocarbon conversion reaction where the hydrogen halide can promote the ionic liquid catalyzed hydrocarbon conversion reaction and reduce the amount of other hydrogen halide, alkyl halide, or metal halide that needs to be added to the method. In one embodiment, the hydrogen halide is hydrogen chloride.

In one embodiment, the light fraction that is stripped out of the outflow from the reactor used for the contacting is treated in whole or in part, in a treater, to remove aromatics prior to being recycled. The treatment used to remove aromatics could include reactive extraction or absorption, such as by contacting the light fraction with a carbon absorber such as activated carbon. Removing the aromatics in the light fraction can be useful if, for example, the aromatics will interfere with the ionic liquid catalyzed hydrocarbon conversion reaction to which the light fraction is recycled. The treatment can reduce the aromatics in the light fraction to zero to 50 wppm, or from zero to 20 wppm. In one embodiment, when activated carbon is used to treat the light fraction the activated carbon will have a capacity for absorbing aromatics of from 40-60 wt %, and the activated carbon will have a service life from eight months to two years.

Regenerating the Ionic Liquid Catalyst

In one embodiment, the method for making hydrocarbon products with reduced organic halide contamination additionally comprises: separating the ionic liquid catalyst from the finished hydrocarbon product to make a separated ionic liquid catalyst, regenerating the separated ionic liquid catalyst in an ionic liquid treater to make a regenerated ionic liquid catalyst having zero to 500 wppm of aromatic hydrocarbons, and recycling the regenerated ionic liquid catalyst to the ionic liquid catalyzed hydrocarbon conversion reaction. In one embodiment, the regenerating is done in a catalyst regeneration step that is also used for regenerating the used ionic liquid catalyst for use in the ionic liquid catalyzed hydrocarbon conversion reaction. One process used for regenerating ionic liquid catalysts is hydrogenation.

Hydrogenation

Hydrogenation is a reduction reaction which results in an addition of hydrogen to a starting molecule. Hydrogenation changes the physical and chemical properties of the starting molecule. The addition of hydrogen can cleave the starting molecule, remove undesired impurities (e.g., sulfur, oxygen, nitrogen, or conjunct polymer), or cause the starting molecule to undergo rearrangement (e.g., isomerization). Hydrogenation is often performed in the presence of a hydrogenation catalyst. One use of hydrogenation is to hydrogenate a used alkylation catalyst, such as a used acidic ionic liquid alkylation catalyst.

In one embodiment, an ionic liquid catalyst becomes deactivated during use and requires regeneration. The deactivation can be caused by, for example, the build-up of conjunct polymer in the alkylation catalyst. Regeneration can be achieved in a hydrogenation reactor (also referred to herein as a hydroregeneration reactor). The hydrogenation removes the impurities, such as conjunct polymer, from the ionic liquid catalyst, thus increasing the acidity and ability of the catalyst to perform alkylations and other hydrocarbon conversion reactions. In this embodiment, the hydrogenation reactor is used to regenerate the ionic liquid catalyst.

In one embodiment, the ionic liquid catalyst is regenerated in the hydrogenation reactor. The hydrogenation reactor contacts the ionic liquid catalyst with hydrogen and typically, a hydrogenation catalyst to regenerate the ionic liquid catalyst.

In one embodiment, zeolites or molecular sieves are added to the hydrogenation catalyst to improve the catalyst's performance. In one embodiment, the hydrogenation catalyst is supported. Typical support materials for the hydrogenation catalyst are kieselguhr, alumina, silica, and silica-alumina. Other support materials include alumina-boria, silica-alumina-magnesia, silica-alumina-titania and materials obtained by adding zeolites and other complex oxides thereto. When used, the support material has adequate mechanical strength and chemical stability at the hydrogenation reaction temperature.

In one embodiment, the hydrogenation is carried out in the presence of a catalyst which usually comprises a metal or non metal hydrogenation component on a porous support material, such as a natural clay or a synthetic oxide. Examples of metal hydrogenation components that can be used are Fe, Co, Ni, Ru, Rh, Pd, Pt, Ir, Os, Cr, Mn, Ti, V, Zr, Mo, W, and mixtures thereof. Examples of non metal hydrogenation components are Te, As, and mixtures thereof. The hydrogenation components can be used singly or in combination.

The hydrogenation can be carried out over a broad range of hydrogen pressures, typically from about 50 to 5,000 psig. Hydrogenation conditions can include temperatures of −20° C. to 400° C., or 50° C. to 300° C.; and total pressures of atmospheric to 5,000 psig, or 50 to 2,500 psig. Hydrogenation contact times can be from 0.1 minute to 24 hours, such as 10 minutes to 12 hours. Feed to catalyst ratios during the hydrogenation can vary from 0.1 to 10 vol/vol/hour. A normal hydrocarbon can optionally be used as a solvent in the hydrogenation reactor.

Examples of hydrogenation of ionic liquid catalysts for regeneration, for example, are given in U.S. patent application Ser. No. 13/563,385, filed Jul. 31, 2012, and U.S. Pat. No. 7,691,771, U.S. Pat. No. 7,651,970, U.S. Pat. No. 7,678,727, and U.S. Pat. No. 7,825,055.

EXAMPLES

Example 1

A solution of hexane contaminated with 0.1 wt % mixed halides (pentyl-, t-butyl, etc) was prepared. The chloride content for the solution of hexane contaminated with mixed halides was measured at 1286 wppm. The solution of contaminated hexane was inserted dropwise into a reaction vessel that was a glass three-neck round bottom flask holding a neat mixture of toluene and either AlCl3 or N-butyl pyridinium heptachloro dialuminate ionic liquid (IL) catalyst. The three-neck round bottom flask was equipped with a pressure-equalizing dropping funnel AlCl3 and the IL catalyst were both strong Lewis acids. Different equivalents of the strong Lewis acids and toluene in respect to the amount of mixed halides were tested. The reactions were performed over a stir plate, and under a stream of nitrogen passing through the reaction vessel. The reactions were performed at room temperature (RT). The nitrogen stream and gases formed in the reactions were passed through pure deionized water in order to trap the hydrochloric acid released through the electophilic aromatic substitution. After the complete insertion of the contaminated hexanes into the reaction vessel, the biphasic mixture was stirred for a few hours (3 hr to 24 hr) at room temperature (20° C. to 25° C.). No noticeable heat was generated during the reaction. After the appropriate amount of time, the biphasic solution was allowed to separate into a catalyst phase and a hydrocarbon phase. Nitrogen gas was bubbled for 30 mins directly into the hydrocarbon phase in order to remove the hydrochloric acid. In one experiment, the gas flow was subsequently passed through a second container filled with 10 ml of pure deionized water. The deionized water and the separated hydrocarbon phase in the reaction vessel were analyzed for chloride content. The chloride content in the separated hydrocarbon phase was determined by gas chromatography and X-ray fluorescence on a XOS Chlora bench-top analyzer. The chloride content in the aqueous phase was determined by ion chromatography, using ASTM D432-11, Standard Test Method for Anions in Water by Suppressed Ion Chromatography.

The results of the chloride analyses are shown below.

| Reagents | Conditions | Chloride in Hydrocarbon Phase | Chloride in Aqueous Phase |
|---|---|---|---|
| AlCl$_3$ (20 eq), toluene (50 eq) | RT, 4 hr | 1.94 wppm | — |
| IL (20 eq), toluene (50 eq) | RT, 4 hr | 1.90 wppm | — |
| IL (20 eq), toluene (50 eq) | RT, 5 hr | 1.18 wppm | 1130 wppm |
| IL (2 eq), toluene (5 eq) | RT, 3 hr | 10.28 wppm | — |
| IL (2 eq), toluene (5 eq) | RT, 24 hr | 11.3 wppm | — |

The contacting of the contaminated hexanes with toluene and either of the strong Lewis acids greatly reduced the organic halide level in the hexanes. The recovery of the majority of the chlorides (i.e., HCl) in the aqueous phase confirmed that electrophilic aromatic substitution according to the Friedel-Crafts reaction had occurred.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

It is claimed:

1. A method for making hydrocarbon products with reduced organic halide contamination, comprising:
   a. separating an effluent from an ionic liquid catalyzed hydrocarbon conversion reaction into:
      i. a hydrocarbon fraction comprising an organic halide contaminant and from greater than zero to less than 5000 wppm olefins; and
      ii. a used ionic liquid catalyst fraction comprising a used ionic liquid catalyst; and
   b. contacting the hydrocarbon fraction with an aromatic hydrocarbon reagent and an ionic liquid catalyst wherein the contacting reduces a level of the organic halide contaminant to from greater than zero to 5 wppm in a finished hydrocarbon product; wherein the ionic liquid catalyst is composed of at least a metal halide compound and an organic salt and the hydrocarbon fraction comprises gasoline blending components, jet fuels, kerosenes, or mixtures thereof.

2. The method of claim 1, wherein the hydrocarbon fraction comprises from 50 to 5000 wppm of the organic halide contaminant.

3. The method of claim 1, wherein the level of the organic halide contaminant is from greater than zero to 3 wppm in the finished hydrocarbon product.

4. A method for making hydrocarbon products with reduced organic halide contamination, comprising:
   a. separating an effluent from an ionic liquid catalyzed hydrocarbon conversion reaction into:
      i. a hydrocarbon fraction comprising an organic halide contaminant and from greater than zero to less than 5000 wppm olefins; and
      ii. a used ionic liquid catalyst fraction comprising a used ionic liquid catalyst; and
   b. contacting the hydrocarbon fraction with an aromatic hydrocarbon reagent and an ionic liquid catalyst wherein the contacting reduces a level of the organic halide contaminant to from greater than zero to 5 wppm in a finished hydrocarbon product, and wherein the contacting is done in a fixed bed reactor and the hydrocarbon fraction comprises gasoline blending components, jet fuels, kerosenes, or mixtures thereof.

5. The method of claim 4, wherein the fixed bed reactor provides a longer residence time for the ionic liquid catalyst than for a mixture of the hydrocarbon fraction and the aromatic hydrocarbon reagent.

6. The method of claim 4, wherein the ionic liquid catalyst is supported on a fixed bed of solid contact material that is wetted by the ionic liquid catalyst and the ionic liquid catalyst is replaced either intermittently or continuously by:
  a. adding a fresh ionic liquid catalyst to the fixed bed of solid contact material, and
  b. withdrawing a partially passivated ionic liquid catalyst.

7. The method of claim 6, wherein the fixed bed reactor provides a longer residence time for a supported liquid catalyst than for a mixture of the hydrocarbon fraction and the aromatic hydrocarbon reagent.

8. The method of claim 1, wherein the aromatic hydrocarbon reagent and the hydrocarbon fraction are mixed together to make a mixed feed and the mixed feed is fed to a reactor used for the contacting.

9. The method of claim 1, wherein the aromatic hydrocarbon reagent is added to a mixture of the hydrocarbon fraction and the ionic liquid catalyst either before or during the contacting.

10. The method of claim 1, wherein the finished hydrocarbon product has from 0 to 5,000 wppm aromatics.

11. The method of claim 1, additionally comprising passing the finished hydrocarbon product to an aromatics absorber, wherein a content of aromatics in the finished hydrocarbon product is reduced to from 0 wppm to 25 wppm.

12. The method of claim 1, wherein a temperature of the hydrocarbon fraction at a start of the contacting is 0° C. to 200° C.

13. A method for making hydrocarbon products with reduced organic halide contamination, comprising:
  a. separating an effluent from an ionic liquid catalyzed hydrocarbon conversion reaction into:
    i. a hydrocarbon fraction comprising an organic halide contaminant and from greater than zero to less than 5000 wppm olefins; and
    ii. a used ionic liquid catalyst fraction comprising a used ionic liquid catalyst; and
  b. contacting the hydrocarbon fraction with an aromatic hydrocarbon reagent and an ionic liquid catalyst wherein the contacting reduces a level of the organic halide contaminant to from greater than zero to 5 wppm in a finished hydrocarbon product, and wherein the hydrocarbon fraction is withdrawn hot from the bottom of a fractionator and the hydrocarbon fraction comprises gasoline blending components, jet fuels, kerosenes, or mixtures thereof.

14. A method for making hydrocarbon products with reduced organic halide contamination, comprising:
  a. separating an effluent from an ionic liquid catalyzed hydrocarbon conversion reaction into:
    i. a hydrocarbon fraction comprising an organic halide contaminant and from greater than zero to less than 5000 wppm olefins; and
    ii. a used ionic liquid catalyst fraction comprising a used ionic liquid catalyst; and
  b. contacting the hydrocarbon fraction with an aromatic hydrocarbon reagent and an ionic liquid catalyst wherein the contacting reduces a level of the organic halide contaminant to from greater than zero to 5 wppm in a finished hydrocarbon product, additionally comprising stripping out a light fraction comprising hydrogen halide from an outflow from a reactor used for the contacting, wherein the hydrocarbon fraction comprises gasoline blending components, jet fuels, kerosenes, or mixtures thereof.

15. The method of claim 14, wherein the light fraction is recycled to the ionic liquid catalyzed hydrocarbon conversion reaction.

16. The method of claim 15, wherein the light fraction is treated to remove aromatics prior to being recycled.

17. The method of claim 1, or claim 4, or claim 13, or claim 14, wherein the ionic liquid catalyzed hydrocarbon conversion reaction is an alkylation, an oligomerization, or a mixture thereof.

18. The method of claim 1, wherein the aromatic hydrocarbon reagent comprises monocyclic aromatic hydrocarbon compounds.

19. The method of claim 1, wherein the aromatic hydrocarbon reagent comprises reformate.

20. The method of claim 1, wherein 0.3 to 20 equivalents of the aromatic hydrocarbon reagent relative to an organic chloride contaminant in the hydrocarbon fraction are mixed together.

21. The method of claim 1, wherein a time for contacting the hydrocarbon fraction is from 2 seconds to 45 minutes.

22. The method of claim 1, wherein a time for contacting the hydrocarbon fraction is 0.1 minutes to 6 hours.

23. The method of claim 1, or claim 4, or claim 13, or claim 14, wherein the used ionic liquid catalyst and the ionic liquid catalyst used for contacting comprise a same cation.

24. The method of claim 1, wherein the ionic liquid catalyst used for contacting is a partially passivated ionic liquid catalyst.

25. The method of claim 1, wherein the ionic liquid catalyst used for contacting has a lower acidity than a more acidic ionic liquid catalyst used in the ionic liquid catalyzed hydrocarbon conversion reaction.

26. A method for making hydrocarbon products with reduced organic halide contamination, comprising:
  a. separating an effluent from an ionic liquid catalyzed hydrocarbon conversion reaction into:
    i. a hydrocarbon fraction comprising an organic halide contaminant and from greater than zero to less than 5000 wppm olefins; and
    ii. a used ionic liquid catalyst fraction comprising a used ionic liquid catalyst; and
  b. contacting the hydrocarbon fraction with an aromatic hydrocarbon reagent and an ionic liquid catalyst wherein the contacting reduces a level of the organic halide contaminant to from greater than zero to 5 wppm in a finished hydrocarbon product, additionally comprising separating the ionic liquid catalyst from the finished hydrocarbon product to make a separated ionic liquid catalyst, regenerating the separated ionic liquid catalyst to make a regenerated ionic liquid catalyst having zero to 500 wppm of aromatic hydrocarbons, and recycling the regenerated ionic liquid catalyst to the ionic liquid catalyzed hydrocarbon conversion reaction, wherein the hydrocarbon fraction comprises gasoline blending components, jet fuels, kerosenes, or mixtures thereof.

27. The method of claim 26, wherein the regenerating is done in a catalyst regeneration step that is also used for regenerating the used ionic liquid catalyst for use in the ionic liquid catalyzed hydrocarbon conversion reaction.

28. The method of claim 1, wherein the finished hydrocarbon product is a gasoline blending component, a jet fuel, a kerosene, or a mixture thereof.

29. The method of claim 1, wherein the contacting is done at a temperature from 0° C. to 40° C.

30. The method of claim 1, wherein a sub-stoichiometric amount of the aromatic reagent relative to the level of the organic halide contaminant is used during the contacting.

* * * * *